United States Patent
Harper et al.

[11] Patent Number: 6,042,539
[45] Date of Patent: Mar. 28, 2000

[54] VACUUM-ACTUATED TISSUE-LIFTING DEVICE AND METHOD

[75] Inventors: Kevin A. Harper, Mason; William D. Fox, New Richmond; Jill E. Sackman, Mason, all of Ohio

[73] Assignee: Ethicon Endo-Surgery, Inc., Cincinnati, Ohio

[21] Appl. No.: 09/277,337

[22] Filed: Mar. 26, 1999

[51] Int. Cl.$^7$ .................................................... A61B 1/22
[52] U.S. Cl. ............................................................ 600/201
[58] Field of Search ................................. 600/201, 208, 600/235, 237; 606/119, 123

[56] References Cited

U.S. PATENT DOCUMENTS

| | | |
|---|---|---|
| 4,633,865 | 1/1987 | Hengstberger et al. . |
| 5,183,033 | 2/1993 | Wilk . |
| 5,309,896 | 5/1994 | Moll et al. . |
| 5,318,012 | 6/1994 | Wilk . |
| 5,353,785 | 10/1994 | Wilk . |
| 5,361,752 | 11/1994 | Moll et al. . |
| 5,398,671 | 3/1995 | Ortiz et al. . |
| 5,402,772 | 4/1995 | Moll et al. . |
| 5,415,159 | 5/1995 | Ortez et al. . |
| 5,415,160 | 5/1995 | Ortiz et al. . |
| 5,425,357 | 6/1995 | Moll et al. . |
| 5,450,843 | 9/1995 | Moll et al. . |
| 5,454,367 | 10/1995 | Moll et al. . |
| 5,465,711 | 11/1995 | Moll et al. . |
| 5,501,653 | 3/1996 | Chin . |
| 5,505,689 | 4/1996 | Kramer et al. . |
| 5,514,075 | 5/1996 | Moll et al. . |
| 5,520,609 | 5/1996 | Moll et al. . |
| 5,522,790 | 6/1996 | Moll et al. . |
| 5,527,264 | 6/1996 | Moll et al. . |
| 5,531,856 | 7/1996 | Moll et al. . |
| 5,545,123 | 8/1996 | Ortiz et al. . |
| 5,562,603 | 10/1996 | Moll et al. . |
| 5,569,165 | 10/1996 | Chin et al. . |
| 5,575,759 | 11/1996 | Moll et al. . |
| 5,601,592 | 2/1997 | Weng . |
| 5,613,939 | 3/1997 | Failla . |
| 5,632,761 | 5/1997 | Smith et al. . |
| 5,634,883 | 6/1997 | Chin et al. . |
| 5,643,178 | 7/1997 | Moll et al. . |
| 5,676,636 | 10/1997 | Chin . |
| 5,681,341 | 10/1997 | Lunsford et al. . |
| 5,690,607 | 11/1997 | Chin et al. . |
| 5,716,326 | 2/1998 | Dannan . |
| 5,716,327 | 2/1998 | Warner et al. . |
| 5,836,871 | 11/1998 | Wallace et al. . |
| 5,853,395 | 12/1998 | Crook et al. . |
| 5,893,368 | 4/1999 | Sugerman . |
| 5,906,577 | 5/1999 | Beane et al. ............................ 600/208 |

FOREIGN PATENT DOCUMENTS 1180932  2/1970  United Kingdom .

*Primary Examiner*—Gene Mancene
*Assistant Examiner*—Eduardo C. Robert
*Attorney, Agent, or Firm*—Matthew S. Goodwin

[57] ABSTRACT

A vacuum-actuated tissue-lifting device and method for performing a surgical procedure in an operative space of a patient are disclosed. The preferred device has a shell with a profile configured to surround a tissue surface of the patient, a vacuum port located on the shell for applying a vacuum between the shell and the tissue surface, and an air conduit extending through the shell to permit air to pass into the operative space of the patient when vacuum is applied. In a preferred embodiment, the device has an entry port located on the shell and a perforable membrane located on the entry port to provide a seal when a surgical instrument is inserted through the membrane during the procedure. The device and method of the invention eliminate the need for carbon dioxide insufflation, mechanical lifting devices which create obstructions and high stress zones on tissues within the operative space created, and unwanted displacement of internal organs when the targeted tissue surface is lifted.

15 Claims, 13 Drawing Sheets

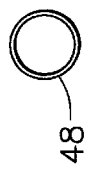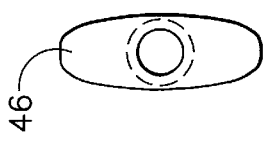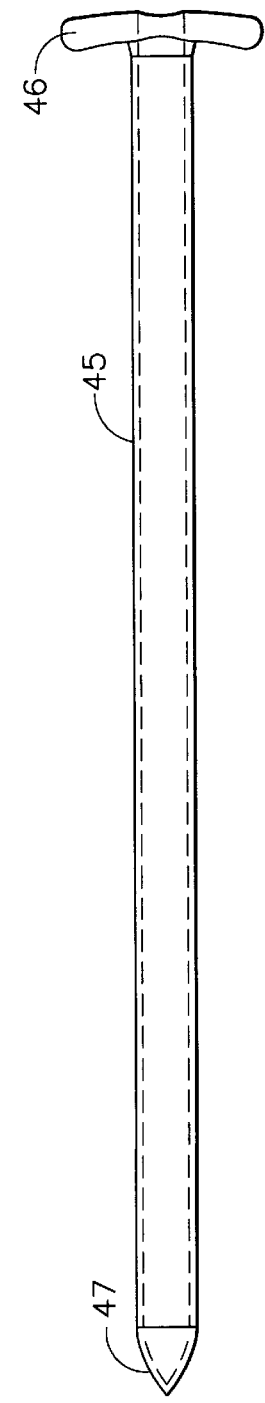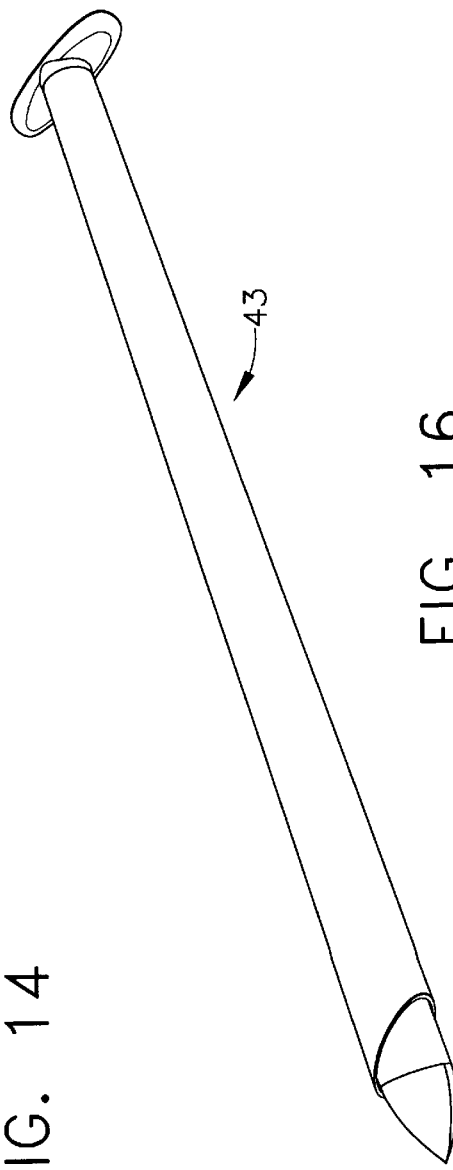

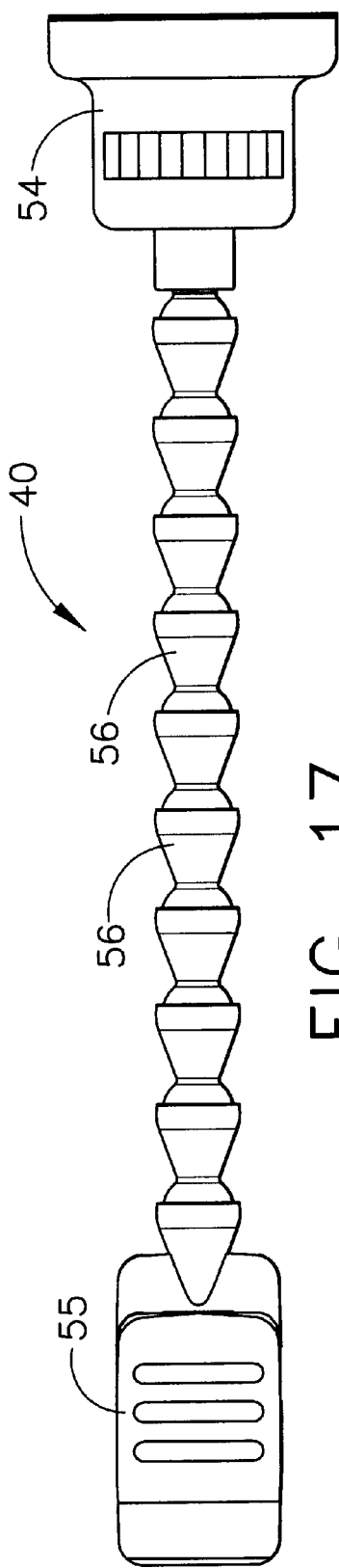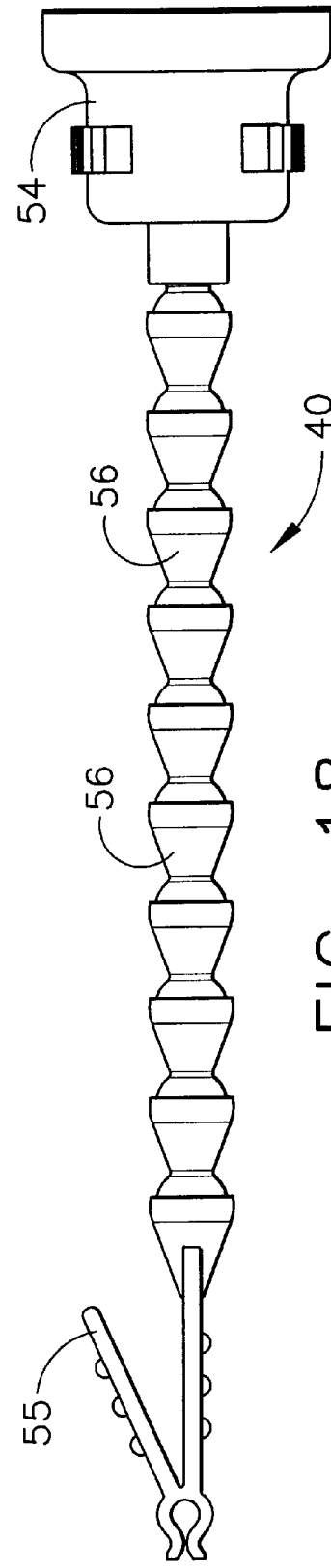

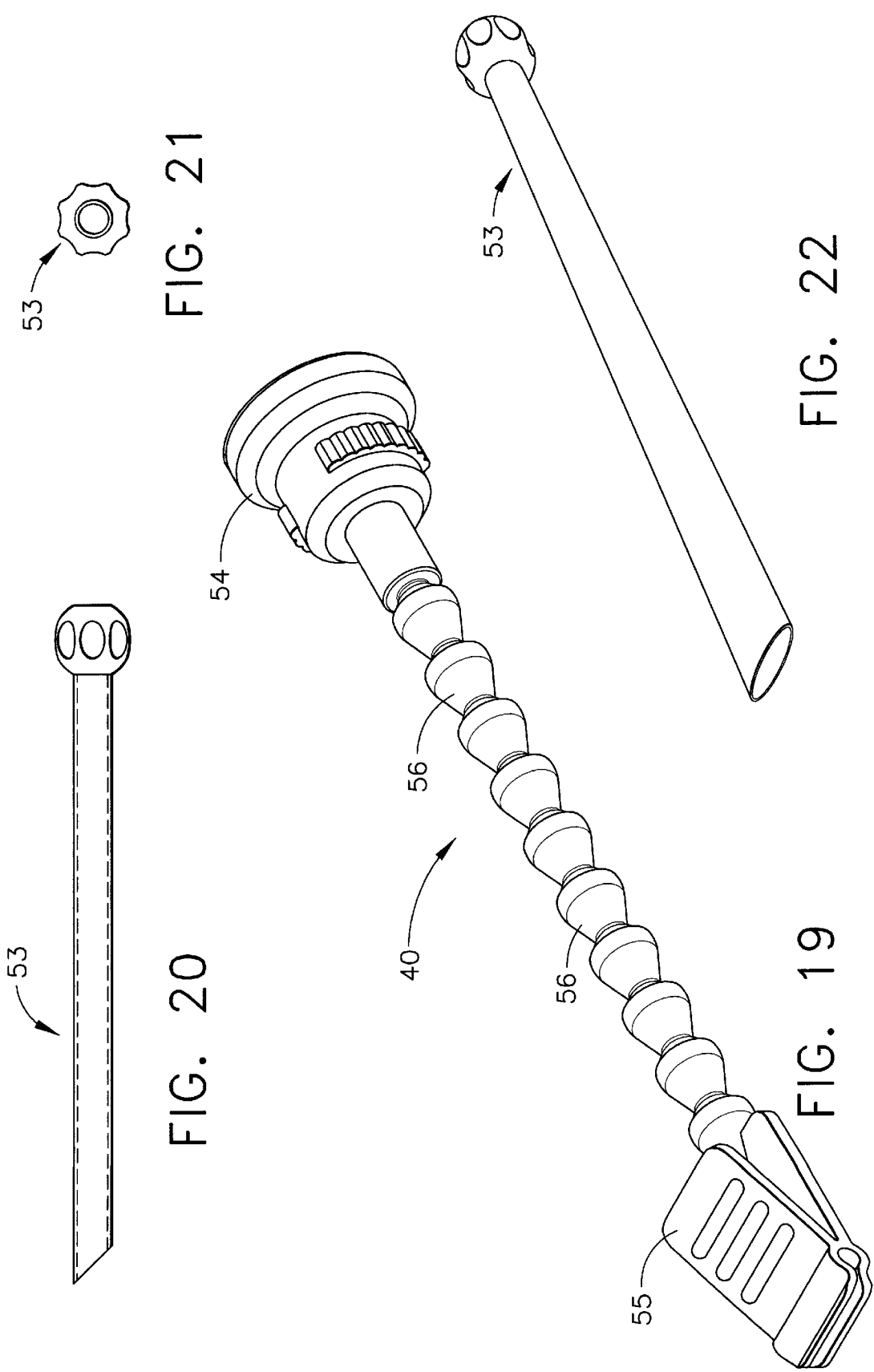

VACUUM-ACTUATED TISSUE-LIFTING DEVICE AND METHOD

BACKGROUND OF THE INVENTION

This invention relates to a surgical device for lifting tissue to create an operative space in a patient for facilitating the performance of a surgical procedure. It also relates to a method of performing a surgical procedure within the patient using a surgical device to create or enlarge the operative space.

During conventional endoscopic surgery, the abdominal cavity of the patient is inflated to provide an operative space between the surgical site and adjacent bodily organs. In the conventional procedure, carbon dioxide gas is pumped into the abdominal cavity to raise the abdominal wall and create the operative space necessary to carry out the endoscopic procedure. Once the abdominal cavity is sufficiently "insufflated" with carbon dioxide gas, the desired diagnostic or therapeutic procedure can be performed with the use of instruments capable of the desired surgical manipulations at the surgical site. These instruments are sealed to prevent or minimize the escape of insufflation gas during the procedure.

Although carbon dioxide insufflation has provided an acceptable methodology for creating an operative space in the abdominal cavity during endoscopic surgery, it does have its drawbacks. When the insufflation gas is pumped into the abdominal cavity, it is pumped into the cavity at a pressure higher than that of the atmosphere in the room. This creates a positive pressure differential between the gas inside the abdominal cavity and the ambient room atmosphere, consequently exerting a force on the internal tissue structures within the abdominal cavity. The disadvantages of this phenomenon during the surgical procedure include the following:

a) pressure on the vena cava can reduce cardiac output, b) pressure on the diaphragm can cause phrenic nerve irritation and reduced respiratory function, c) carbon dioxide absorption may increase the need for ventilation, d) potential hypercarbia and blood acidosis in respiratory compromised patients, and e) tissue desiccation and cooling due to the dry cold gas present in the abdominal cavity.

There are other practical limitations with the use of carbon dioxide insufflation as well. These include the expense of the system for storing and pumping the gas into the abdominal cavity, and the difficulties when using suction during the surgical procedure to c lea r smoke or fluids from the operative site. Unfortunately, when suction is used inside the abdominal cavity for those purposes, it will naturally remove the carbon dioxide gas, decreasing the positive pressure inside the abdomen, thus sometimes causing a loss in the proper lift of the abdominal wall.

In view of the drawbacks attendant with carbon dioxide insufflation during endoscopic surgery, alternatives to this methodology have been proposed. In particular, numerous patents have been published which describe various mechanical lifts which are designed to elevate the abdominal wall during an endoscopic procedure to create the operative space. Examples of patents in this area are U.S. Pat. Nos. 5,309,896; 5,361,752; 5,402,772; 5,425,357; 5,450,843; 5,454,367; 5,465,711; 5,501,653; 5,505,689; 5,514,075; 5,520,609; 5,522,790; 5,527,264; 5,531,856; 5,562,603; 5,569,165; 5,575,759; 5,632,761; 5,634,883; 5,643,178; 5,676,636; 5,681,341; 5,690,607; 5,716,327 and 5,836,871.

The mechanical wall lift devices described in these patents typically are initially inserted into the abdominal cavity, and then actuated to physically lift the interior tissue surfaces of the abdominal wall. In certain illustrated embodiments, balloon structures are designed to inflate inside the abdominal cavity and lift the interior abdominal wall. These balloon structures act like car jacks to separate the abdominal wall from the internal tissues. In other embodiments, "fan blade" style retractors operate by means of an external lifting mechanism, such as a mechanical lifting arm. The fan blades are attached to the lifting arm and then inserted into the abdominal cavity. The arm is then activated and then pushes against the abdominal wall to lift it.

Other examples of patents describing devices which mechanically lift the abdominal wall to provide an operative space include U.S. Pat. Nos. 5,398,671; 5,415,159; 5,415, 160; 5,545,123; 5,183,033; 5,318,012; 5,353,785; 5,601, 592; 5,716,326 and 5,613,939.

Although the mechanical wall lifting devices provide an alternative to conventional carbon dioxide insufflation, these devices have some significant drawbacks. A major drawback is that these devices must be initially deployed in the interior abdominal cavity and then actuated to lift the abdominal wall for creating the operative space. Unfortunately, these devices tend to be bulky and can create a significant obstruction in the cavity for the surgeon, thus making the performance of the desired operative procedure at the surgical site more difficult. The mechanical devices also require a bulky hoist mechanism that must be attached to the operating table or other support structure, or a surgical assistant must hold the abdomen up using direct upward muscular force. Further, the mechanical devices create less operative space than is needed to complete many surgeries because the space created with these devices is shaped more like a "tent" than a dome.

With respect to the mechanical devices which include an inflatable balloon, once the balloon is inflated, it will create direct pressure on internal tissue structures within the abdominal cavity. This direct pressure can cause problems, for example, reduced blood flow, or a reduction in excursion of the diaphragm with respiration. The "fan blade" retractor designs and methods apply a force near the incision site on the abdominal wall. The tissue surface area affected by the fan blade is small, thus significantly increasing the contact stress on the tissue, and potentially resulting in tissue damage.

Another device for lifting the abdominal wall to create an operative space within the abdominal cavity is described in U.S. Pat. No. 4,633,865. This device uses vacuum to lift the abdominal wall to perform examinations and surgical interventions within the abdominal cavity. The device consists of a cowling that is hermetically sealed against the exterior abdominal wall. The cowling has a central opening with an annular projection directed inwardly. The opening is temporarily closed using a lid, and vacuum is applied between the inner surface of the cowling and the exterior abdominal wall, causing the abdominal wall to be raised toward the cowling. With the wall raised toward the cowling, the lid over the central opening is removed and the abdominal wall can then be pierced. Subsequently, the lid covering the opening in the cowling can be removed, and instruments may be inserted through the opening, and into the abdominal cavity for examination and surgical interventions.

Although this device eliminates the need for carbon dioxide insufflation and represents an alternative to the mechanical wall lifts which must be deployed within the interior of the abdominal cavity, it has some significant drawbacks. The most significant drawback is that when the abdominal wall is lifted upon application of vacuum, the internal organs within the abdominal cavity will lift upwardly in tandem with the upward movement of the abdominal wall. This is so because a negative pressure develops in the abdominal cavity when the vacuum is applied to the exterior wall. As a result of this negative pressure created in the abdominal cavity, the internal organs will be displaced, and consequently lifted upwardly as the abdominal wall is lifted. As a result, the internal organs do not fall away and will remain positioned adjacent the abdominal wall. Consequently, the desired operative space between the abdominal wall and the internal organs for effectively carrying out the endoscopic surgical procedure will not be provided, and serious injury to these internal organs may occur during the surgical procedure if the required operative space is not created.

Another drawback to the vacuum-assisted device illustrated in U.S. Pat. No. 4,633,865 is that it does not describe an adequate mechanism for maintaining a vacuum seal to ensure adequate abdominal lift when a surgical instrument is inserted through the opening in the cowling and into the abdominal cavity during the endoscopic surgical procedure.

In view of the deficiencies inherent in the prior art devices for lifting the abdominal wall during an endoscopic surgical procedure to create an operative space, a device is needed which will address these inherent deficiencies. Specifically, the device and its method of use will eliminate the requirement for carbon dioxide insufflation of the abdominal cavity. Additionally, it will not create obstructions or barriers within the interior operative space, thus reducing surgeon inconvenience and patient risk. Further, the ideal device will lift the desired tissue without creating unwanted displacement of internal organs, ensuring that appropriate space between the lifted tissue and the internal organs is created. This ideal instrument would also preferably have the capability to provide and maintain lift even when surgical instruments or human digits are inserted through it to reach the surgical site, and the ability to have internal organs temporarily externalized through it while maintaining lift. Further, the ideal device will have at least one receptacle which is suitable for attaching and holding the various surgical instruments (including cameras) which the surgeon may employ, freeing the hands of the surgeon or assistant. Finally, it would certainly be advantageous if such a device were created which could be employed using less expensive surgical instruments which do not require seals to maintain an insufflated abdominal space or other operative space during the surgical procedure.

SUMMARY OF THE INVENTION

In one aspect, the invention is a vacuum-actuated tissue-lifting device for creating an operative space in a patient during a surgical procedure. The device comprises a shell, a vacuum port located on the shell, and an air conduit extending through the shell.

The shell of the tissue-lifting device is composed of a material substantially impermeable to air. The shell has a profile configured to surround a tissue surface of the patient. The shell has a contacting edge adapted to seal the device against the tissue surface of the patient. The shell defines an expansion cavity between the shell and the tissue surface of the patient prior to application of vacuum.

The vacuum port on the shell is in communication with the expansion cavity. When vacuum is applied through the vacuum port, the tissue surface of the patient is lifted into the expansion cavity toward the shell.

The air conduit extends through the shell and the tissue surface into the operative space of the patient. The air conduit is adapted to permit passage of air exteriorly of the patient into the operative space of the patient. When vacuum is applied through the vacuum port to lift the tissue surface toward the shell, air passes through the air conduit into the operative space to allow internal tissues of the patient to separate from the lifted tissue surface during the surgical procedure.

In another aspect of the invention, the invention is a method for performing a surgical procedure in an operative space of a patient. In the practice of the method, a vacuum-actuated tissue-lifting device is provided. The device comprises a shell and a vacuum port located on the shell. The shell is composed of a material substantially impermeable to air. It has a profile configured to surround the tissue surface of the patient. The shell has a contacting edge adapted to seal the device to the tissue surface of the patient. The shell defines an expansion cavity between the shell and the tissue surface of the patient prior to application of vacuum. The vacuum port is in communication with the expansion cavity. When vacuum is applied through the vacuum port, the tissue surface of the patient is lifted into the expansion cavity toward the shell.

The method comprises the steps of positioning the contacting edge of the shell of the tissue-lifting device onto the tissue surface of patient; applying a vacuum through the vacuum port of the tissue-lifting device so as to lift the tissue surface of the patient toward the shell of the device; providing an air passage exteriorly of the patient into the operative space of the patient while vacuum is applied; inserting a surgical instrument into the operative space of the patient through the shell of the tissue-lifting device and the tissue to be lifted; and using the surgical instrument in the operative space of the patient so as to perform the surgical procedure.

In a preferred embodiment of the invention, the tissue-lifting device of this invention has at least one entry port located on the shell, and a perforable membrane located on the entry port. In another preferred embodiment, an attachment receptacle is located on the shell to attach and hold surgical instruments which are required to perform the desired procedure.

The entry port provides an entry passageway exteriorly of the patient into the operative space of the patient when the tissue surface is penetrated. The perforable membrane blocks the passageway to substantially prevent passage of air into the expansion cavity when vacuum is applied through the vacuum port. The perforable membrane is conformable to, and sealingly engaged with, a surgical instrument inserted through the membrane and into the passageway of the entry port to minimize passage of air into the expansion cavity while using the surgical instrument in the operative space of the patient during the surgical procedure.

The device of this invention, and the method of this invention for performing a surgical procedure in an operative space of a patient, eliminate the requirement for carbon dioxide insufflation to lift the tissue surface of the patient for creating space for an operative procedure. The need for insufflation is eliminated because it is unnecessary to pump carbon dioxide gas into the desired operative space with the device or the method of this invention to lift the tissue surface.

Further, the device of this invention, and the method of this invention for performing a surgical procedure in an operative space of a patient, do not require the deployment of a mechanical lift within an interior operative space, which would undesirably create a barrier or obstruction for the surgeon during the operative procedure. In contrast to the mechanical lift devices which push against the interior tissue surfaces inside the operative space, the device of this invention is actuated using vacuum exteriorly of the desired operative space to lift the targeted tissue surfaces upwardly. Not only are obstructions or barriers avoided, but pressure points or stress areas resulting from contact of the mechanical lifting mechanisms with the targeted tissue surfaces are also avoided.

Significantly, the device of this invention in a preferred embodiment includes an air conduit extending through the shell for permitting passage of air exteriorly of the patient into the operative space of the patient. Consequently, when vacuum is applied through the vacuum port on the shell of the device, air passes through the air conduit into the operative space. This is important to eliminate the negative pressure which would otherwise be created within the targeted operative space as vacuum is applied to the expansion cavity between the shell and the tissue surface. Since negative pressure is avoided, tissues within the operative space of the patient will not be lifted upwardly in tandem with the tissue surface as it moves upwardly in response to the application of vacuum. As a result, a separation between the lifted tissue surface and tissues within the operative space is created, and a suitable operative space for the surgical procedure consequently can be established.

Similarly, the method of this invention for performing the surgical procedure specifies providing an air passage exteriorly of the patient into the operative space of the patient while vacuum is applied to ensure that undesirable displacement of internal organs of the patient does not occur. The air passage may be created prior to or during the application of vacuum. An air conduit may be used for creating the passage. If a conduit were used, then it may be inserted directly through the tissue layers. Alternatively, it could be inserted through the shell of the device and the tissue layers, or introduced internally through a surgical instrument, such as an endoscope, which is inserted into the operative space during the procedure.

In addition, the device in another preferred embodiment of this invention has an entry port located on the shell and a perforable membrane located on the entry port. Significantly, the perforable membrane is conformable to, and sealingly engaged with, a surgical instrument which is inserted through the membrane. Consequently, the perforable membrane located on the entry port will maintain an adequate vacuum seal to lift the tissue surface during the surgical procedure. Importantly, this seal will be maintained when an instrument is inserted through the perforable membrane because of the conformable nature of the membrane.

The device of this invention, and the method of this invention for performing a surgical procedure, can be used in any open or endoscopic surgical procedure, although the invention is especially targeted toward endoscopic applications. The device and method can be used, for example, during the removal of a gall bladder, hernia repair and endoscopic harvesting procedures, particularly procedures directed to the harvesting of the sapheinous vein for use as a coronary artery bypass graft. Other examples include, but are not limited to, laparoscopic assisted vaginal hysterectomy, neck surgery, oophorectomy, tubal ligation, splenectomy, Nissen fundoplication, vagotomy, nephrectomy, appendectomy, colectomy, organ biopsy, and exploratory laparotomy.

BRIEF DESCRIPTION OF THE DRAWINGS

FIG. 12 is a side elevational view of the optical trocar cannula used in conjunction with providing an air passage into the abdominal cavity as illustrated in FIG. 8.

FIG. 13 is a proximal end elevational view of the cannula of FIG. 12.

FIG. 14 is a side elevation view of the optical trocar obturator illustrated in FIG. 6.

FIG. 15 is a proximal end elevational view of the obturator of FIG. 14.

FIG. 16 is a perspective view of the trocar whose elements are shown in FIGS. 12 and 14.

FIG. 17 is a plan view of the snap-on attachment receptacle shown in FIG. 11.

FIG. 18 is a side elevational view of the snap-on attachment receptacle of FIG. 17.

FIG. 19 is a perspective view of the snap-on attachment receptacle of FIG. 17.

FIG. 20 is a side elevational view of the additional cannula illustrated in FIG. 10.

FIG. 21 is a proximal end elevational view of the cannula of FIG. 20.

FIG. 22 is a perspective view of the cannula of FIG. 20.

DETAILED DESCRIPTION OF THE PREFERRED EMBODIMENTS

Figure 1:
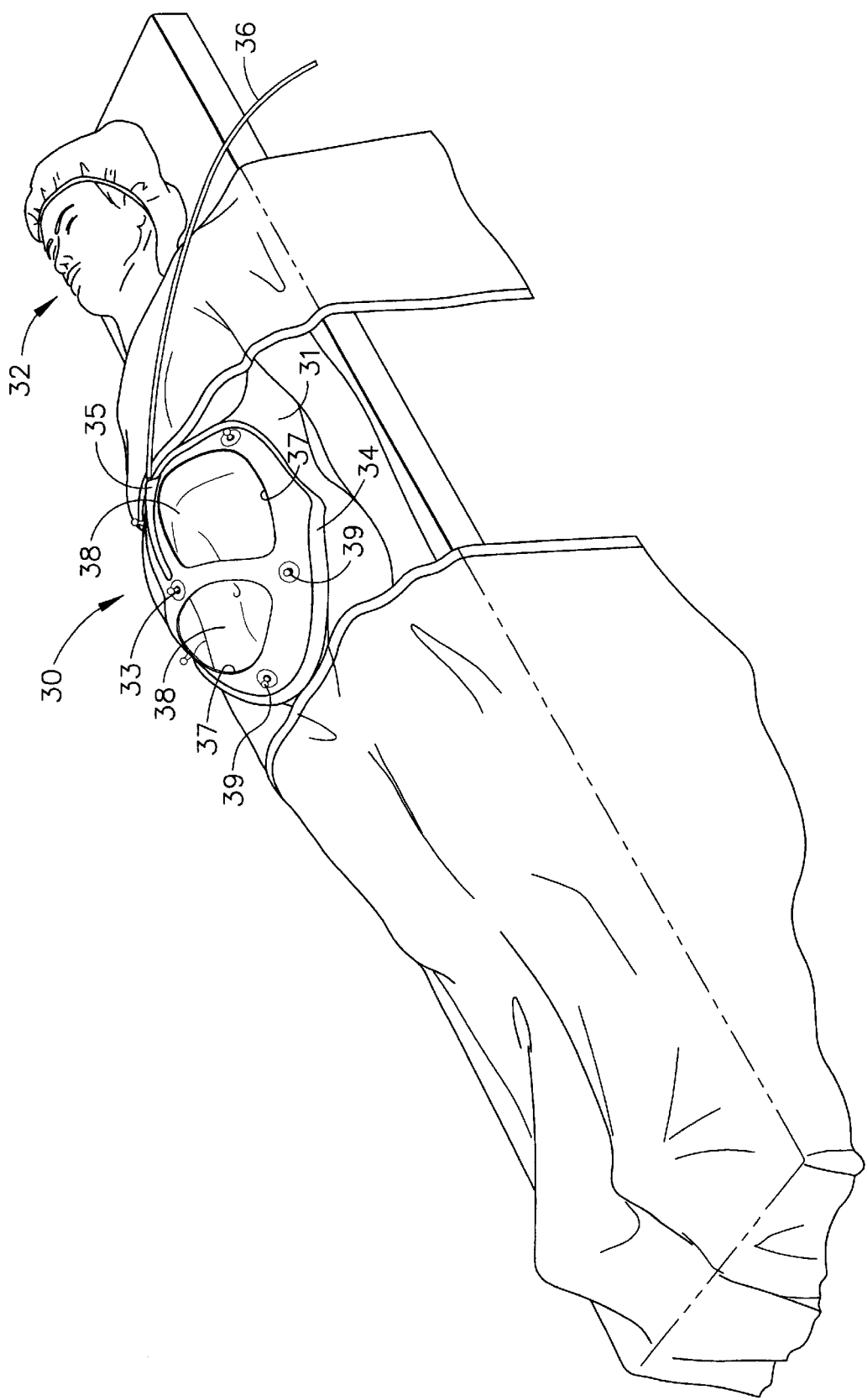
FIG. 1 is a perspective view of a preferred embodiment of the tissue-lifting device of the invention illustrated as it would be used on a surgical patient.
Figure 2:
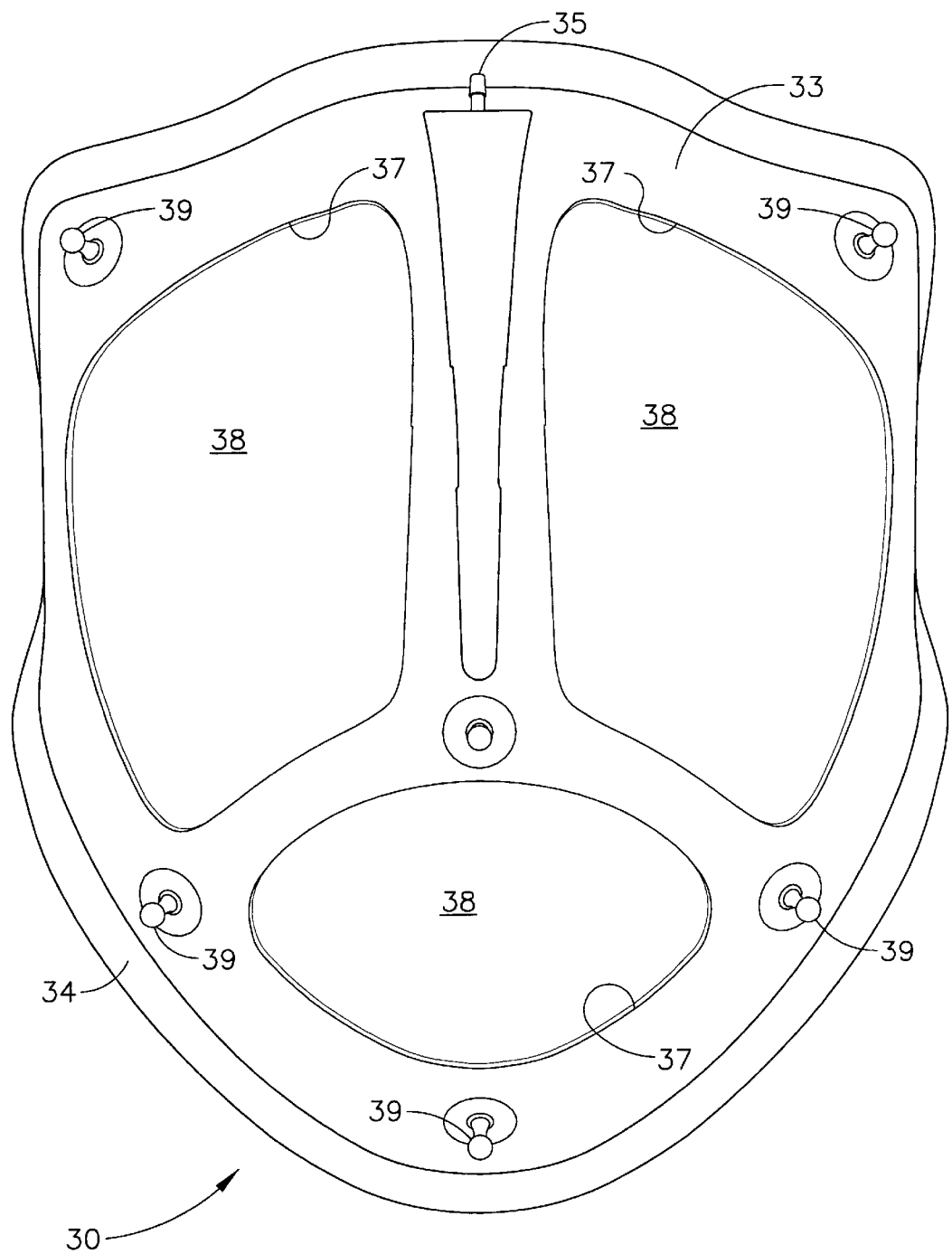
FIG. 2 is a plan view of the device of FIG. 1.
Figure 3:
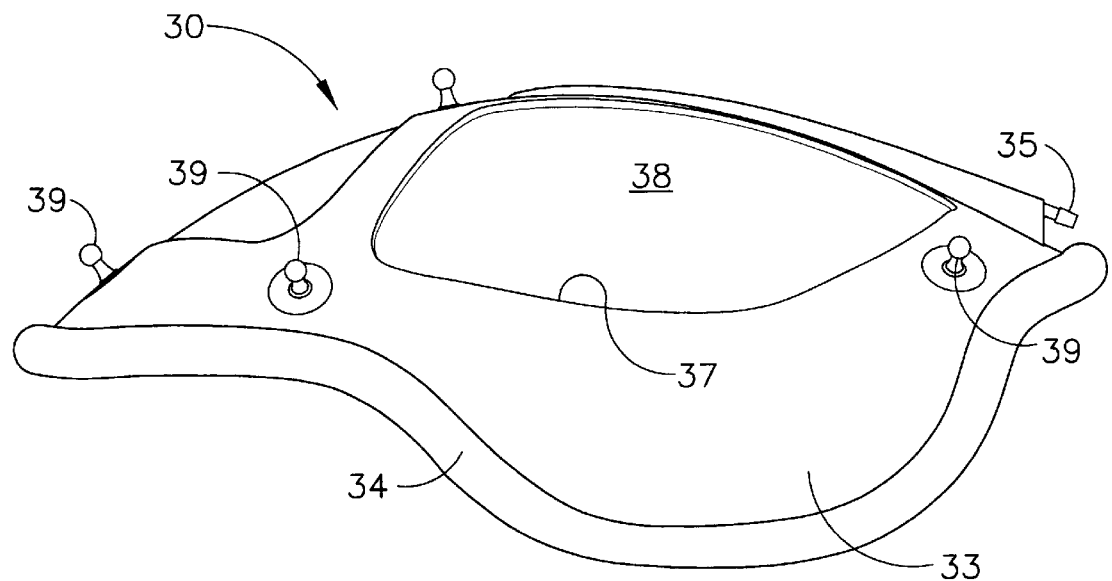
FIG. 3 is a side elevation view of the device of FIG. 1.
Figure 4:
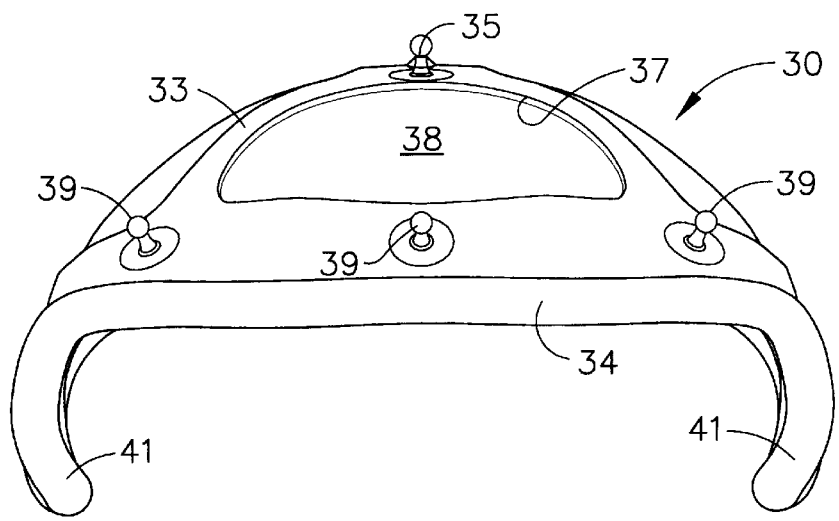
FIG. 4 is an end view of the device of FIG. 1.

Although this invention will be described in connection with its most preferred embodiment as depicted in the figures, the reader will easily recognize that numerous additional embodiments will be well within the scope of the invention defined by the claims which appear below. The detailed description which follows is intended merely to illustrate the preferred aspect of the invention, and is not intended to limit the scope and spirit of the claimed invention in any way. In this regard, certain definitions for the terms used in the claims are appropriate to ensure that the reader will not think to limit the scope of these terms to the specific preferred embodiments described in this detailed description. These definitions are given by way of example only, without limitation.

The term "surgical procedure" means collectively all therapeutic and diagnostic procedures, both open and endoscopic. It also includes "field" surgeries, for example, emergency, remote or mobile procedures for exploratory, therapeutic and diagnostic applications.

The term "operative space" means any working space created in the patient beneath tissue which is lifted using the device of the invention or practicing the method of this invention, including the space created as a result of expanding natural pre-existing separations between tissue planes, or separations which are surgically created.

The term "shell" means any structural member or collection of members which defines the expansion cavity between the member(s) and the tissue surface of the patient prior to application of vacuum.

Now that critical elements of the claimed invention have been defined, we can now turn our attention to the illustrations which accompany this specification to more fully describe the preferred embodiment. Referring initially to FIGS. 1–5, the preferred vacuum-actuated tissue-lifting device 30 of this invention particularly adapted for lifting an external abdominal surface 31 of a human patient 32 is illustrated. The device has an impermeable shell 33, which is configured to conform to the exterior surface of the patient, once the device is positioned on the external surface of the abdominal wall and vacuum is applied.

The shell is advantageously composed of a medical grade, clear molded plastic such as a polycarbonate approved for tissue contact. Other possibilities for the composition of the shell include malleable materials, particularly metals and metal alloys, such as medical grade, annealed stainless steel, aluminum and titanium.

Alternatively, high durometer elastomeric materials, for example polyurethanes, can be used. Optimally, the shell is composed of a material which exhibits the flexibility required to conform to the contour of the patient, yet exhibit the strength needed to support the necessary operating loads during the surgical procedure.

In the embodiment depicted in the figures, the shell is a unitary member. Alternatively, the shell may include multiple members to provide specific properties. Further, the shell may have multiple compartments to isolate various interior sections of the shell if desired. Additionally, the thickness of the shell may vary to provide different physical properties at various positions on the shell. For example, the shell may have reduced thickness at its periphery adjacent the tissue surface to increase the flexibility at the tissue surface and to enhance the sealing capability of the shell when it is positioned on the external tissue surface. In any event, the shell may be designed so that its physical properties are tailored to meet the specific needs of the surgical patient and the particular operative procedure being performed.

Referring again to FIGS. 1–5, the shell has a contacting edge 34 at its outer periphery which initially comes into contact with the exterior surface of the abdominal wall which is desired to be lifted. The contacting edge, when positioned on the exterior tissue surface, is adapted to seal the device against the tissue surface of the patient when vacuum is applied. An elongated vacuum port 35 is positioned mid-line on the shell and provides a vacuum passage through the shell and membrane into the expansion cavity (to be described later in connection with FIG. 7). A tubular conduit 36 is attached to the vacuum port, and the conduit is connected to a vacuum source (not shown).

The insertion and withdrawal of various surgical instruments, including visualization devices such as endoscopes, through the shell of the device is carried out through a plurality of entry ports 37 located on the shell. The entry ports provide an entry passageway through the shell and into the patient at the desired surgical site during the operative procedure. The entry ports each have a perforable membrane 38 located on the entry port. The perforable membranes block the entry passageway to substantially prevent the passage of air through the shell of the device when vacuum is applied through the vacuum port.

The perforable membranes located on the entry ports of the shell may be composed of any material which is substantially impermeable to air and will be conformable to, and sealingly engaged with, a surgical instrument which is inserted through the membrane during the surgical procedure. For example, the membrane may be composed of a medical grade, elastomer such as silicone which exhibits a hardness in the range of 35–60 Shore A durometer. Alternatively, other elastomers which can be used include neoprene, santoprene and polyisoprene. These elastomers may be co-molded to bond to the shell. Alternatively, the membrane may be composed of an elastomer-plastic composite, for example an elastomer backed by a plastic sheet so that the elastomer will conform to seal around an instrument inserted through the membrane, and the plastic sheet will provide the support necessary for the loading exerted on the membrane when instruments are inserted into or withdrawn form the patient. Preferably, the membrane is an elastomer co-molded onto the shell.

Figure 5:
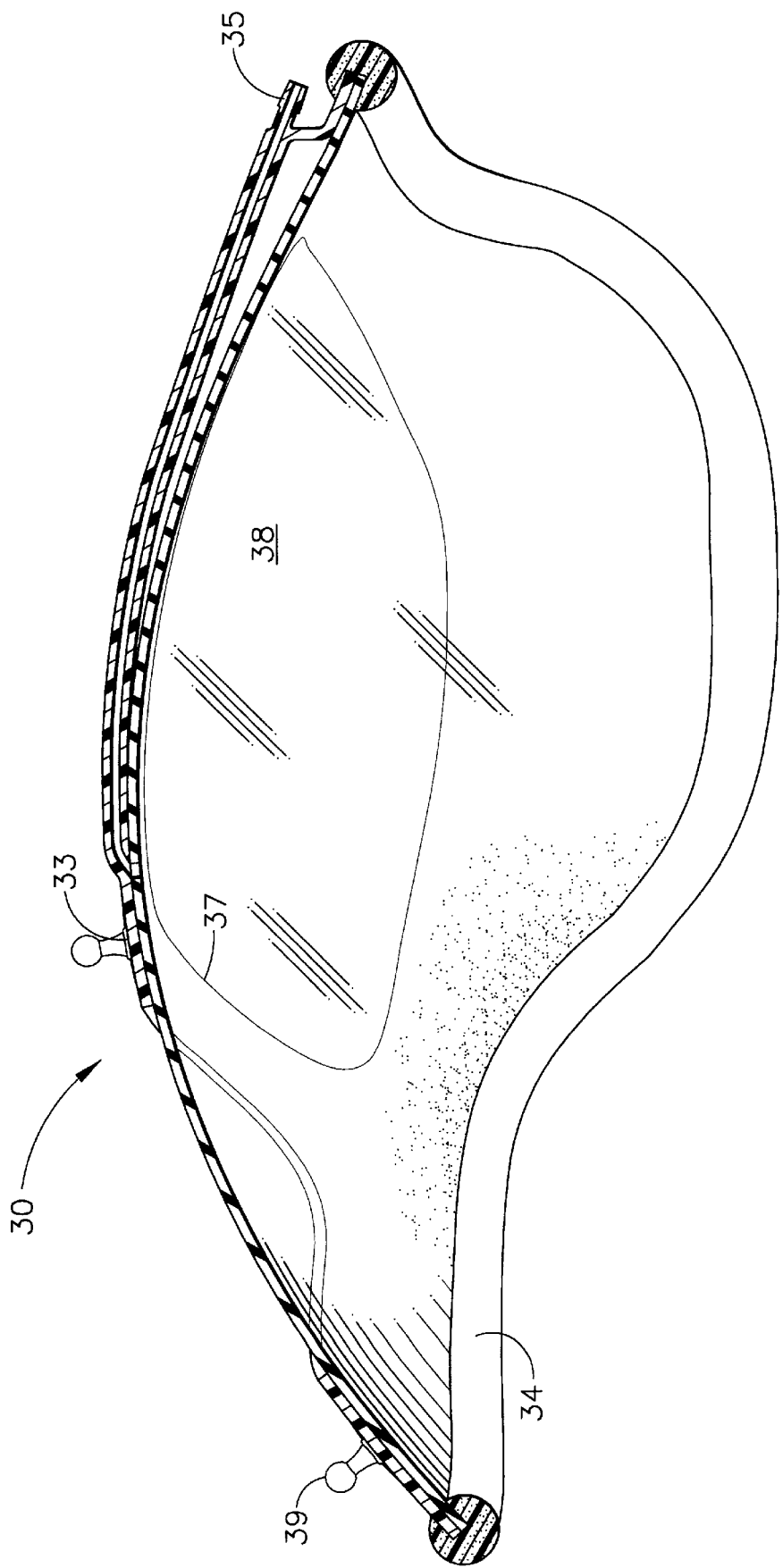
FIG. 5 is a centerline section view of the device of FIG. 1.

In a particularly preferred embodiment, an adhesive backing may be applied to the perforable membrane or, alternatively, it can be applied to the plastic sheet if the membrane is composed of an elastomer-plastic composite. The adhesive backing may be desirable to adhere the tissue to the shell once the exterior tissue surface is lifted to come into contact with the interior surface of the shell. This approach is illustrated in FIG. 5 where the stippled area represents an adhesive coating applied on the interior surface of the shell to maintain contact (and therefore a seal) between the exterior tissue surface and the interior surface of the shell.

Although the perforable membrane is preferably composed of an elastomer or an elastomeric-plastic composite, it may be fabricated from other materials. For example, the membrane may be in the form of a bellowed rubber grommet attached to the shell, a gel-like material or a closed cell foam.

Continuing to refer to FIGS. 1–5, in addition to the entry and vacuum ports, the device also includes a plurality of attachment receptacles 39 located on the shell. Each attachment receptacle is designed to receive an instrument holder 40, for example as depicted in FIGS. 17, 18 and 19, for fixing and maintaining the location of various surgical instruments which are used in conjunction with the device of this invention during the surgical procedure. Finally, it is now worthy to point out that the contacting edge 34 of the shell has a peripheral underlayer 41 extending radially inwardly from the contacting edge to promote the sealing contact between the exterior tissue surface and the shell.

Figure 6:
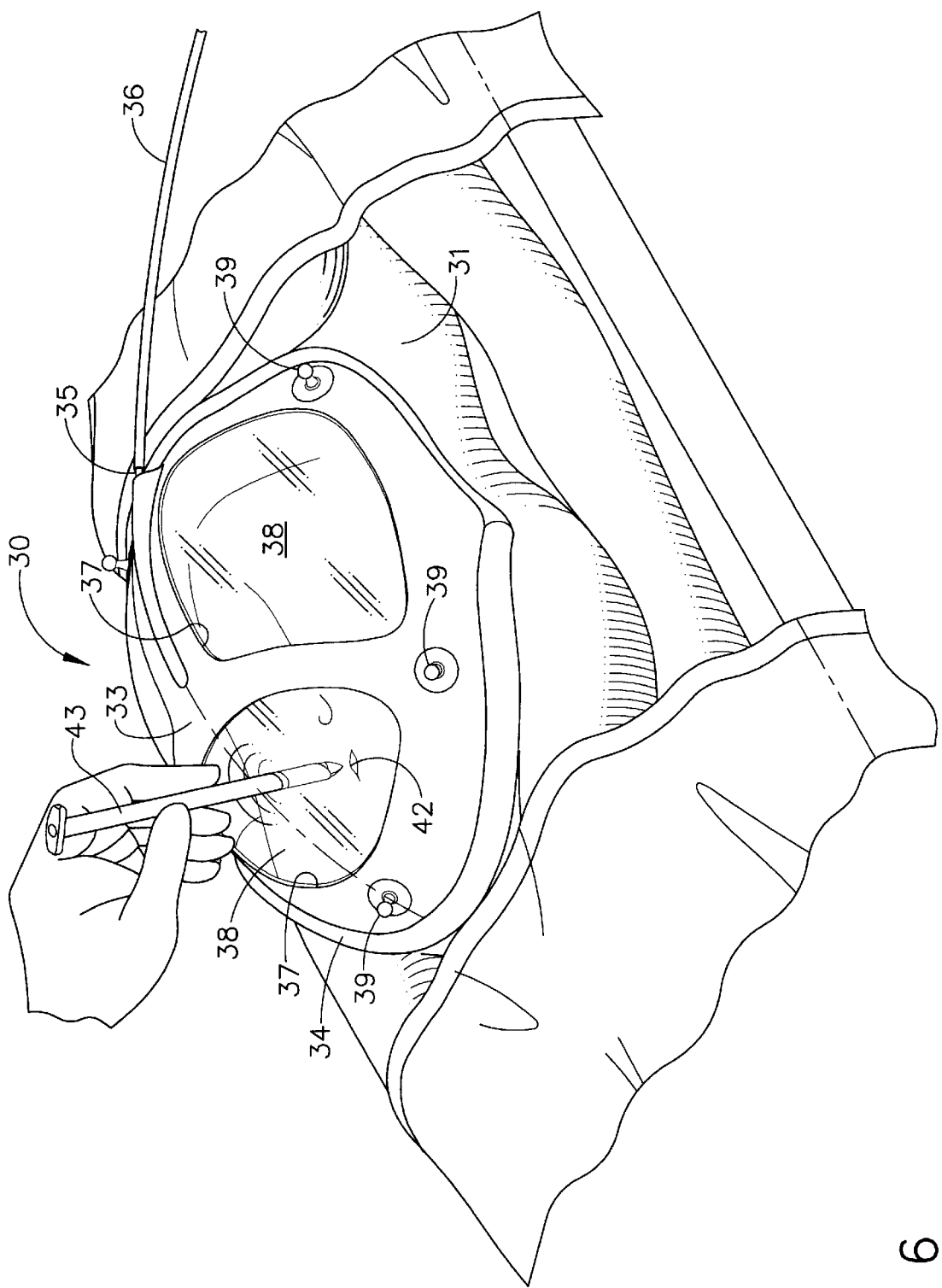
FIG. 6 is a perspective view of the device of FIG. 1 covering a patient exhibiting a previously administered entry incision and illustrating the insertion of an optical trocar through the shell of the device.
Figure 7:
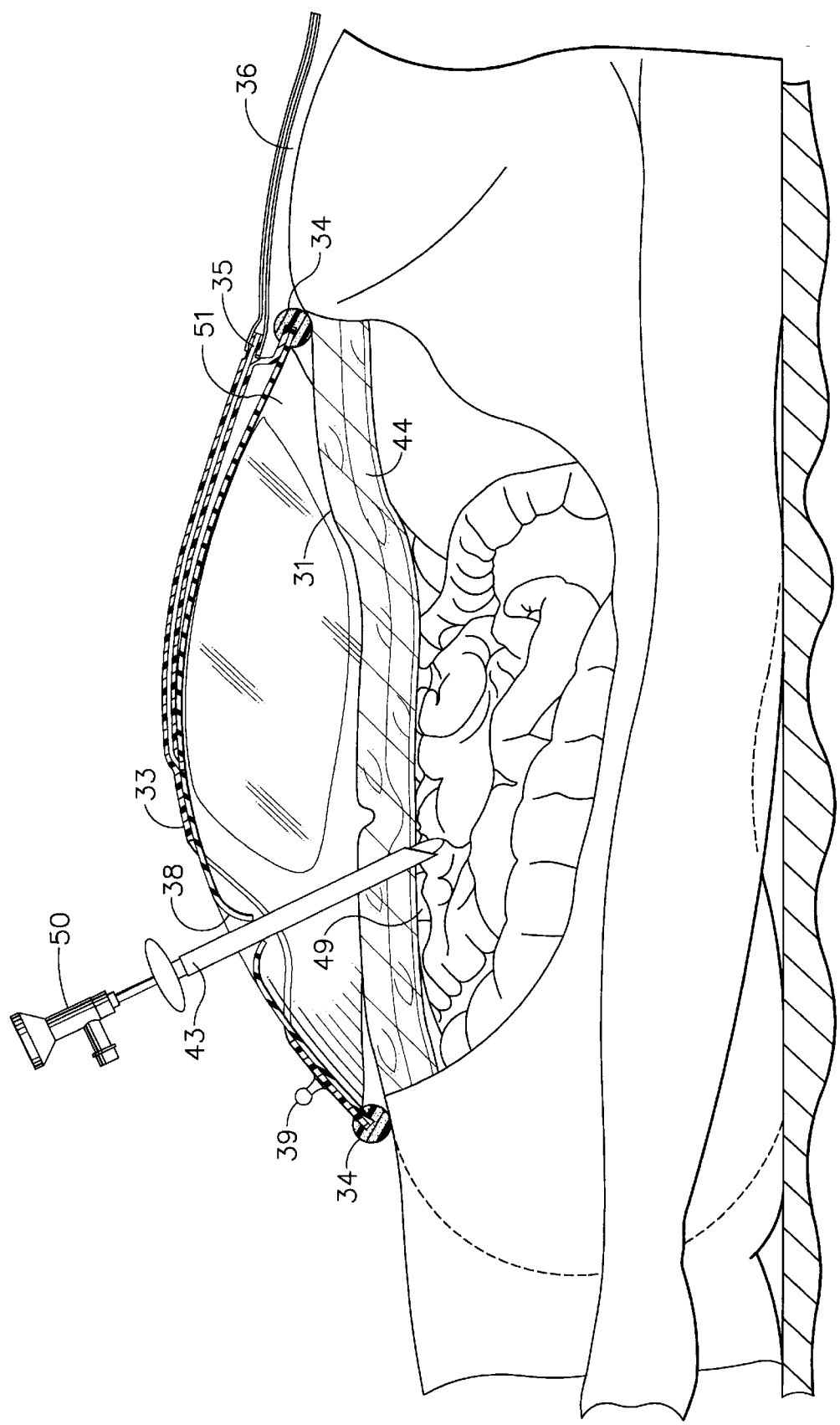
FIG. 7 is a centerline section view of the device of FIG. 1 in conjunction with a side elevation view of a patient, partially in section, illustrating the placement of the trocar through the entry incision of the abdominal wall.

Referring now to FIGS. 6–11, the methodology by which the tissue-lifting device of this invention can be used to create an operative space within the surgical patient is illustrated. Turning initially to FIGS. 6 and 7, the contacting edge of the shell of the device is initially positioned on to the tissue surface of the patient, which in this case is the exterior abdominal surface of the human patient (also depicted nicely in FIG. 1). An entry incision 42 through the exterior abdominal surface of the patient is made, and an optical trocar assembly 43 is inserted through a perforable membrane of one of the entry ports on the shell in the direction of the entry incision. As illustrated in FIG. 7, the perforable membrane conforms nicely to the outer diameter of the trocar assembly. Downward pressure is applied on the trocar assembly to cause a penetration through the various tissue layers 44 of the patient until the obturator has fully penetrated the tissue layers and has entered the interior abdominal cavity under visual guidance from a camera in the optical trocar.

The optical trocar assembly 43 is shown in more detail in FIGS. 12–16. The assembly includes a hollow optical obturator 45 which has a handle 46 for manipulation. The obturator has a transparent tip 47 which is shaped for passage through tissue. The obturator is received in a cannula 48.

As illustrated in FIG. 7, once the optical trocar assembly is properly positioned within the interior abdominal cavity 49, a laparoscope 50 may be inserted through the hollow obturator to observe the interior abdominal cavity during a portion of the minimally invasive surgical procedure. Also noteworthy is that the shell of the device defines an expansion cavity 51 between the exterior abdominal surface 31 of the patient and the interior surface of the shell.

Figure 8:
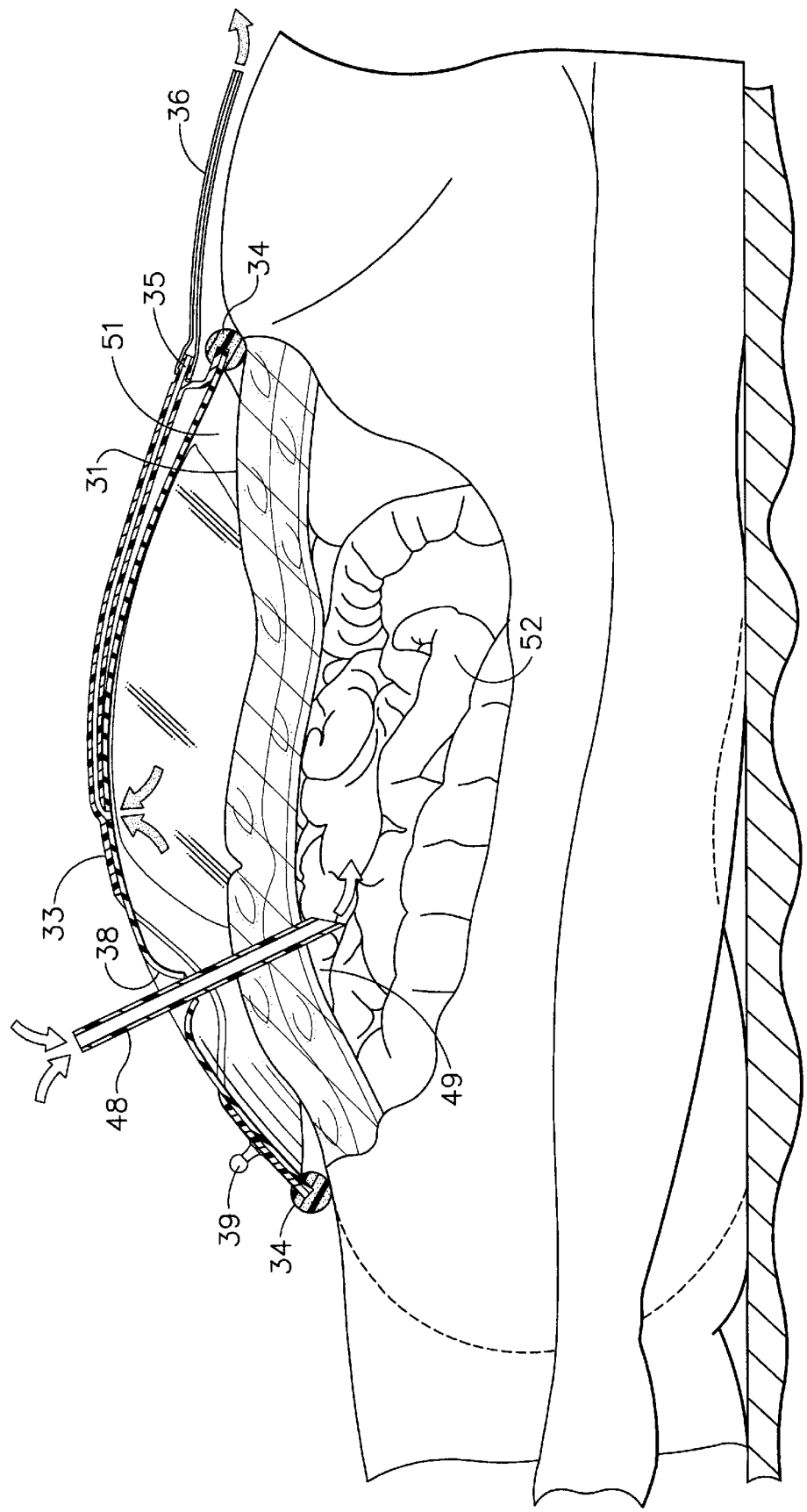
FIG. 8 is a perspective view like FIG. 7 wherein vacuum is applied to the cavity between the shell of the device and the abdominal wall surface of the patient and the trocar cannula acts as an air conduit to equalize the pressure in the abdominal cavity.

Referring now to FIG. 8, the laparoscope and hollow optical obturator are removed from the optical trocar assembly and the cannula 48 is left intact.

Figure 9:
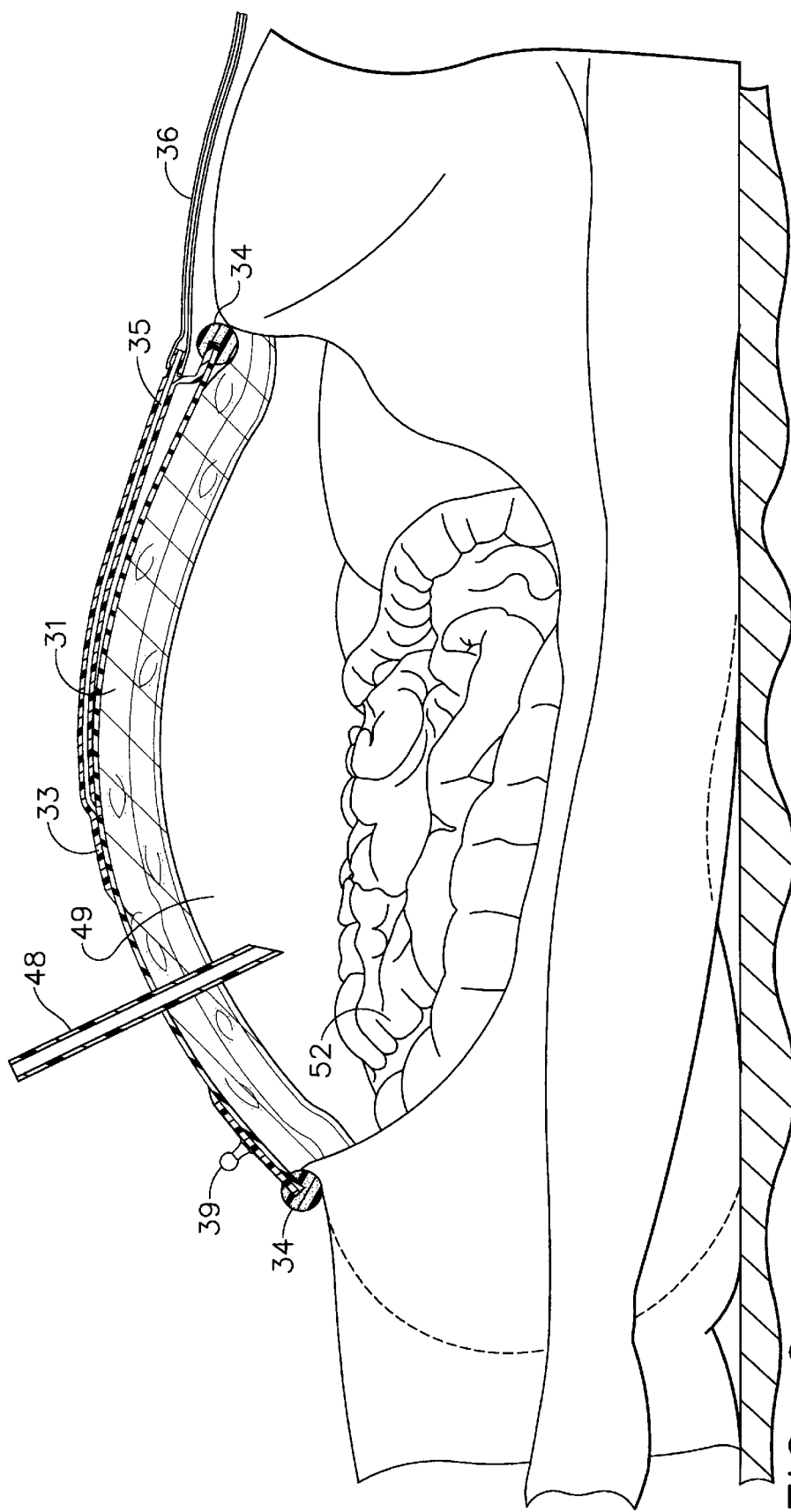
FIG. 9 is a view like FIG. 8 wherein the abdominal wall has risen into contact with the inner surface of the shell of the device.

Significantly, the cannula acts as an air conduit to provide for the passage of air from the operating room into the interior abdominal cavity of the patient. Vacuum is then applied through the vacuum port 35 of the shell, which consequently pulls a vacuum from the expansion cavity, thus lifting the exterior abdominal surface 31 of the patient toward the shell (see the directional arrows for the application of vacuum through the vacuum port). Significantly, as illustrated in FIGS. 8 and 9, as the vacuum is applied to lift the exterior abdominal surface toward the shell, room air will pass through the cannula air conduit into the interior abdominal cavity 49 so that the internal tissues 52 of the patient can separate from the lifted abdominal tissue surface (see the directional arrows at the proximal and distal ends of the cannula air conduit for the passage of air from the operating room into the interior abdominal cavity). In this manner, an operative space in the interior abdominal cavity between the lifted abdominal tissue and the internal tissues of the patient is created for safely performing a surgical procedure.

Figure 10:
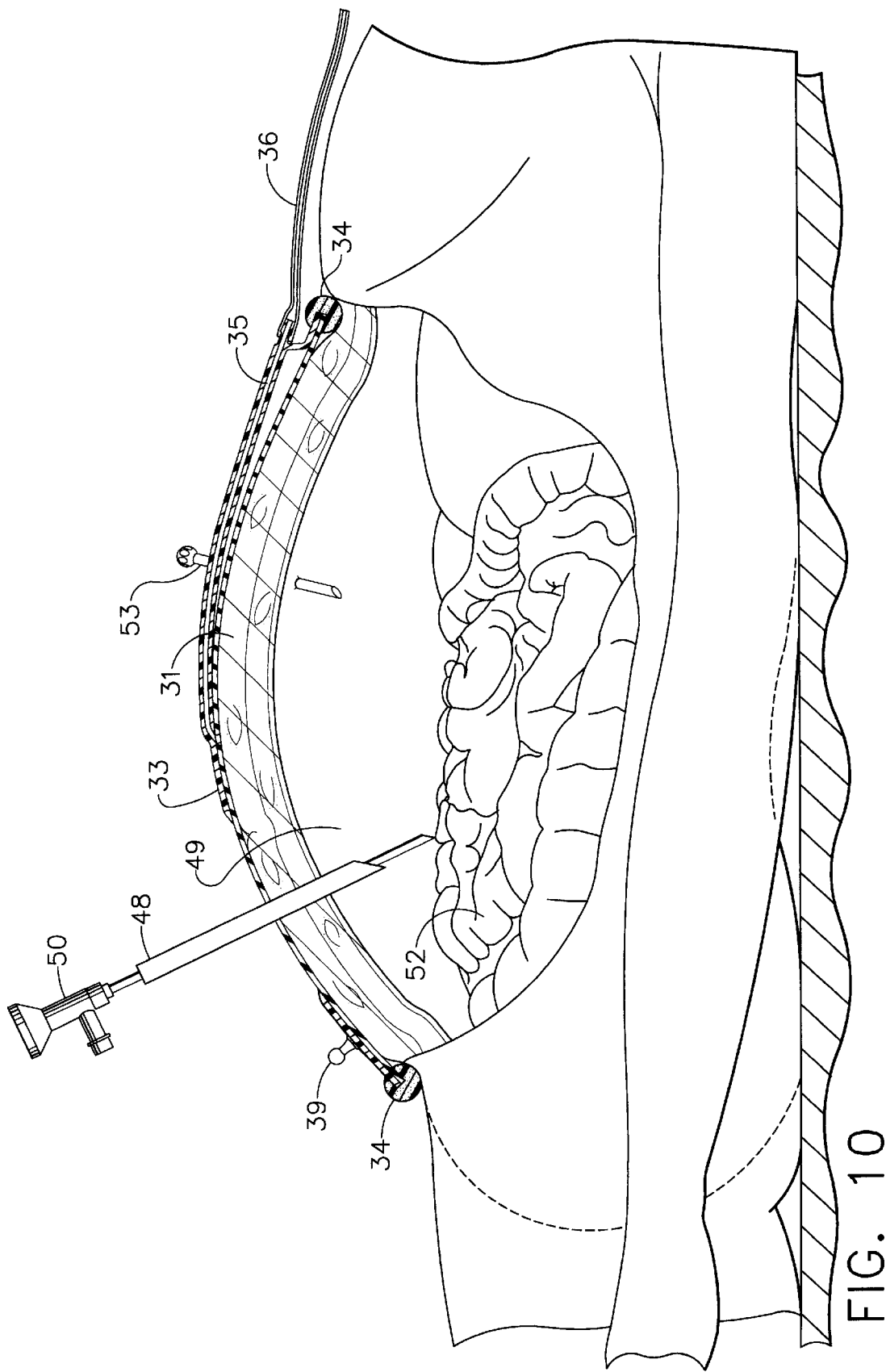
FIG. 10 is a view like FIG. 9 wherein an endoscope has been inserted through the cannula of the trocar. Also illustrated is a second cannula shown projecting through the shell of the device and into the patient's abdominal cavity.
Figure 11:
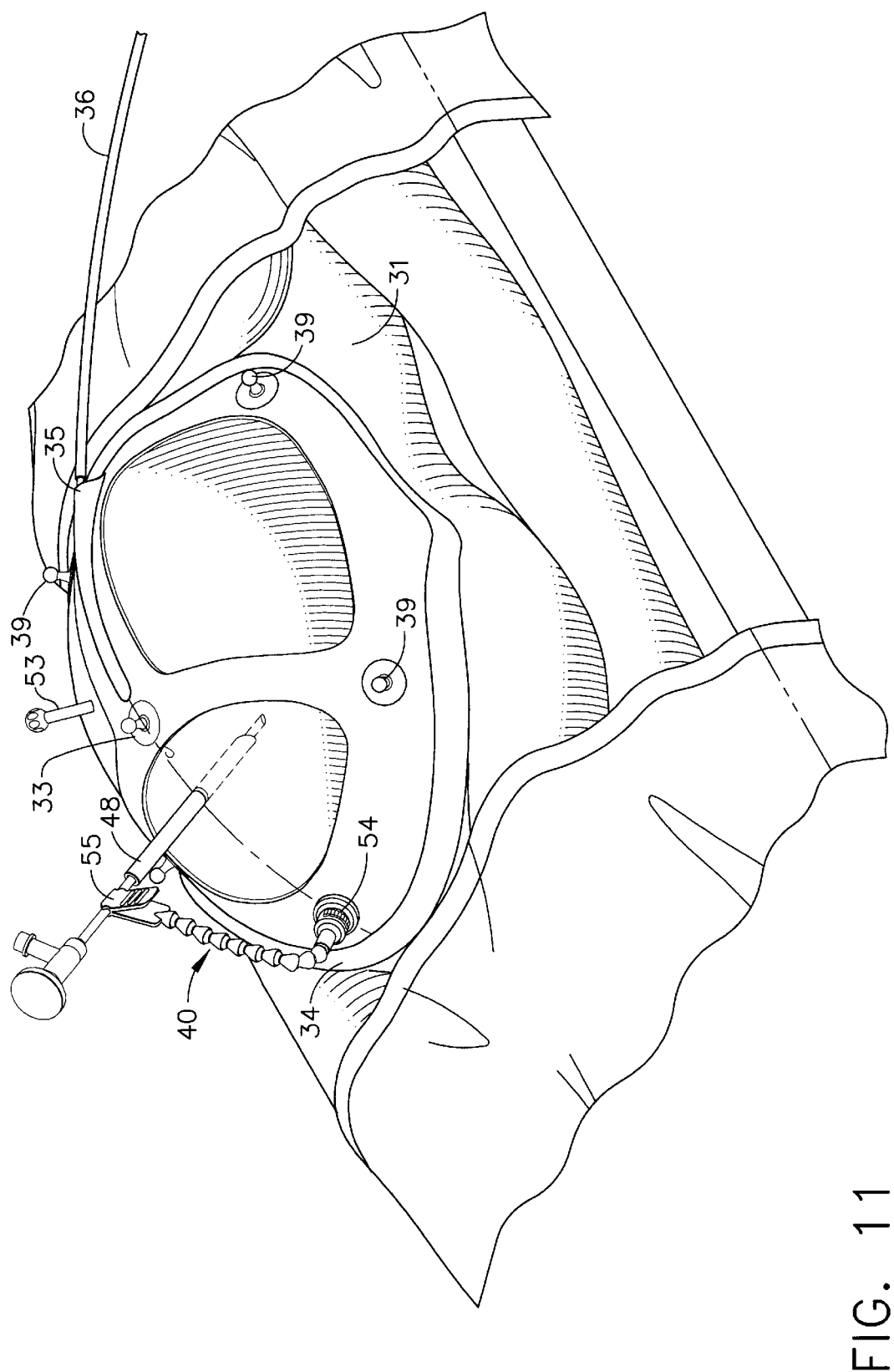
FIG. 11 is a perspective view of a portion of FIG. 1 illustrating an attachment supporting the endoscope which is used during the surgical procedure on the patient.

Referring now to FIGS. 10 and 11, since an adequate operative space has been created in the interior abdominal cavity, a surgical procedure can safely be performed. In these illustrations, the laparoscope 50 has been reinserted into the operative space, and another surgical instrument conduit 53 has been inserted through one of the perforable membranes on the shell to carry out the desired surgical procedure. The instrument conduit 53 is illustrated in more detail in FIGS. 20–22.

FIG. 11 further illustrates the benefits of attaching a flexible instrument holder 40 to one of the attachment receptacles 39 located on the shell. As illustrated in FIGS. 17–19, the instrument holder has a receiving base 54 at its proximal end for mating with the attachment receptacle, and a spring-loaded clip bracket 55 at its distal end for grasping the shaft of a desired surgical instrument, e.g. a laparoscope. A plurality of joint links 56 joins the receiving base at its proximal end to the clip bracket at its distal end. The joint links provide the required degree of flexibility to position the attached surgical instrument at a desired location while maintaining that fixed position during the procedure. Of course, it is envisioned that other instrument holders may be utilized in the practice of the claimed invention. For example, an instrument holder may include a ball turret style locking mechanism to allow rotation of the attached instrument independent of actual movement of the instrument.

What is claimed is:

1. A vacuum-actuated tissue-lifting device for creating an operative space in a patient during a surgical procedure, said device comprising:

a) a shell composed of a material substantially impermeable to air, said shell having a profile configured to surround a tissue surface of the patient, said shell having a contacting edge adapted to seal said device against the tissue surface of the patient, and said shell defining an expansion cavity between said shell and the tissue surface of the patient prior to application of vacuum;

b) a vacuum port located on said shell, said vacuum port being in communication with the expansion cavity, and when vacuum is applied through said vacuum port, the tissue surface of the patient is lifted into the expansion cavity toward said shell; and c) an air conduit means for extending through said shell and the tissue surface into the operative space of the patient, said air conduit means adapted to permit passage of air exteriorly of the patient into the operative space of the patient, and when vacuum is applied through said vacuum port to lift the tissue surface toward said shell, air passes through said air conduit means into the operative space to allow internal tissues of the patient to separate from the lifted tissue surface during the surgical procedure.

2. The device of claim 1 wherein said shell has a peripheral underlayer extending radially from said contacting edge, said peripheral underlayer adapted to further seal said device against the tissue surface of the patient.

3. The device of claim 1 further comprising an attachment receptacle located on said shell.

4. The device of claim 1, further comprising:

a) at least one entry port located on said shell, said entry port providing an entry passageway exteriorly of the patient into the operative space of the patient when the tissue surface is penetrated; and b) a perforable membrane located on said entry port and blocking said passageway to substantially prevent passage of air into said expansion cavity when vacuum is applied through said vacuum port, said perforable membrane being conformable to, and sealingly engaged with, a surgical instrument inserted through said membrane and into said passageway of said entry port to minimize passage of air into said expansion cavity while using said surgical instrument in the operative space of the patient during the surgical procedure.

5. A vacuum-actuated tissue-lifting device for expanding an operative space of a patient during a surgical procedure, said device comprising:
- a) a shell composed of a material substantially impermeable to air, said shell having a profile configured to surround a tissue surface of the patient, said shell having a contacting edge adapted to seal said device against the tissue surface of the patient, and said shell defining an expansion cavity between said shell and the tissue surface of the patient prior to application of vacuum;
- b) a vacuum port located on said shell, said vacuum port being in communication with the expansion cavity, and when vacuum is applied through said vacuum port, the tissue surface of the patient is lifted into the expansion cavity toward said shell;
- c) at least one entry port located on said at least one shell, said entry port providing an entry passageway exteriorly of the patient into the operative space of the patient when the tissue surface is penetrated; and
- d) a perforable membrane located on said entry port at least one and blocking said passageway to substantially prevent passage of air into said expansion cavity when vacuum is applied through said vacuum port, said perforable membrane being conformable to, and sealingly engaged with, a surgical instrument inserted through said membrane and into said passageway of said entry port at least one to minimize passage of air into said expansion cavity while using said surgical instrument in the operative space of the patient during the surgical procedure.

6. The device of claim 5 wherein said shell has a peripheral underlayer extending radially from said contacting edge, said peripheral underlayer adapted to further seal said device to the tissue surface of the patient.

7. The device of claim 5 further comprising an attachment receptacle located on said shell.

8. A method for performing a surgical procedure in an operative space of a patient, said method comprising the steps of:
- a) providing a vacuum-actuated tissue-lifting device, said device comprising:
  - i) a shell composed of a material substantially impermeable to air, said shell having a profile configured to surround a tissue surface of the patient, said shell having a contacting edge adapted to seal said device to the tissue surface of the patient, and said shell defining an expansion cavity between said shell and the tissue surface of the patient prior to application of vacuum;
  - ii) a vacuum port located on said shell, said vacuum port being in communication with the expansion cavity, and when vacuum is applied through said vacuum port, the tissue surface of the patient is lifted into the expansion cavity toward said shell;
- b) positioning said contacting edge of said shell of said tissue-lifting device onto the tissue surface of the patient;
- c) applying a vacuum through said vacuum port of said tissue-lifting device so as to lift the tissue surface of the patient toward said shell of said device;
- d) providing an air passage exteriorly of the patient into the operative space of the patient while vacuum is applied;
- e) inserting a surgical instrument into the operative space of the patient through said shell of said tissue-lifting device; and
- f) using said surgical instrument in the operative space of the patient so as to perform the surgical procedure.

9. The method of claim 8 wherein during the step of providing an air passage, an air conduit is inserted through the tissue surface into the operative space of the patient.

10. The method of claim 9 wherein during the step of inserting the air conduit into the operative space of the patient, the air conduit is inserted through said shell of said tissue-lifting device.

11. The method of claim 8 wherein said tissue-lifting device has: a) at least one entry port located on said shell, said entry port providing a passageway during the step of inserting said surgical instrument into the operative space of the patient; and b) a perforable membrane located on said entry port and blocking said passageway to substantially prevent passage of air into said expansion cavity during the step of applying the vacuum through said vacuum port, said perforable membrane being conformable to, and sealingly engaged with, the surgical instrument inserted therethrough; wherein:

during the step of inserting said surgical instrument into the operative space of the patient, said instrument is inserted through said perforable membrane located on said entry port of said tissue-lifting device to minimize passage of air exteriorly of the patient into said expansion cavity during the surgical procedure.

12. The method of claim 8 wherein the surgical procedure is performed on a human patient.

13. The method of claim 12 wherein the surgical procedure is a minimally invasive surgical procedure.

14. The method of claim 13 wherein said tissue-lifting device is positioned onto an exterior tissue surface of the patient.

15. The method of claim 14 wherein said tissue-lifting device is positioned on an exterior abdominal surface of the patient, and the surgical instrument is used in an interior abdominal cavity of the patient to perform the minimally invasive surgical procedure.

* * * * *